US009751768B2

(12) United States Patent
Mouazer et al.

(10) Patent No.: US 9,751,768 B2
(45) Date of Patent: Sep. 5, 2017

(54) PROCESS FOR EXTRACTING PHOSGENE

(71) Applicant: HUNTSMAN INTERNATIONAL LLC, The Woodlands, TX (US)

(72) Inventors: Rabah Mouazer, Wavre (BE); Arend-Jan Zeeuw, Wassenaar (NL); Robert Henry Carr, Bertem (BE)

(73) Assignee: HUNTSMAN INTERNATIONAL LLC, The Woodlands, TX (US)

( * ) Notice: Subject to any disclaimer, the term of this patent is extended or adjusted under 35 U.S.C. 154(b) by 0 days.

(21) Appl. No.: 15/116,252

(22) PCT Filed: Feb. 10, 2015

(86) PCT No.: PCT/EP2015/052679
§ 371 (c)(1),
(2) Date: Aug. 3, 2016

(87) PCT Pub. No.: WO2015/121211
PCT Pub. Date: Aug. 20, 2015

(65) Prior Publication Data
US 2017/0008771 A1  Jan. 12, 2017

(30) Foreign Application Priority Data
Feb. 12, 2014 (EP) ................................ 14154766

(51) Int. Cl.
*C01B 31/28* (2006.01)
*B01D 53/22* (2006.01)
(Continued)

(52) U.S. Cl.
CPC ............ *C01B 31/28* (2013.01); *B01D 53/228* (2013.01); *B01D 61/246* (2013.01); *B01D 71/26* (2013.01);
(Continued)

(58) Field of Classification Search
USPC ........................................................ 560/347
See application file for complete search history.

(56) References Cited

U.S. PATENT DOCUMENTS 7,584,629 B2    9/2009  Sohn et al.
2007/0012577 A1  1/2007  Bulan et al.
(Continued)

FOREIGN PATENT DOCUMENTS

WO    WO 2005/051841   *  6/2005
WO    WO2013026591     *  2/2013

OTHER PUBLICATIONS

Li ("Review of CO2 absorption using chemical solvents in hollow fiber membrane contactors" Separation and Purification Technology, 41 (2005), p. 109-122).*

*Primary Examiner* — Jafar Parsa
*Assistant Examiner* — Amy C Bonaparte
(74) *Attorney, Agent, or Firm* — Huntsman International LLC; Robert Diaz

(57) ABSTRACT

A process for extracting a phosgene compound, comprising providing a membrane extracting unit comprising at least one extracting cell that comprises at least one membrane contactor module having at least two sides, a gas side and a liquid side; letting an initial gas stream comprising a phosgene compound flow on the gas side of the membrane contactor module; and letting an extractant liquid stream, suitable for dissolving a phosgene compound, flow on the liquid side of the membrane contactor module so that the extractant liquid stream absorbs the phosgene compound from the initial gas stream and provides a second extractant liquid stream enriched with the phosgene compound.

17 Claims, 3 Drawing Sheets

(51) Int. Cl.
*C07C 263/10* (2006.01)
*B01D 61/24* (2006.01)
*B01D 71/26* (2006.01)
*B01D 71/34* (2006.01)
*B01D 71/36* (2006.01)
*B01D 71/70* (2006.01)
*C07C 263/20* (2006.01)

(52) U.S. Cl.
CPC ............. *B01D 71/34* (2013.01); *B01D 71/36* (2013.01); *B01D 71/70* (2013.01); *C07C 263/10* (2013.01); *C07C 263/20* (2013.01); *B01D 2257/93* (2013.01); *B01D 2311/25* (2013.01); *B01D 2325/38* (2013.01); *C07C 2601/14* (2017.05); *Y02P 20/582* (2015.11)

(56) References Cited

U.S. PATENT DOCUMENTS

| | | |
|---|---|---|
| 2011/0257428 A1 | 10/2011 | Knoesche et al. |
| 2012/0251435 A1* | 10/2012 | Lehr .................. C01B 7/04 423/507 |
| 2014/0147373 A1 | 5/2014 | Mouazer et al. |

* cited by examiner

PROCESS FOR EXTRACTING PHOSGENE

CROSS-REFERENCE TO RELATED APPLICATIONS

This application is the National Phase of International Application PCT/EP2015/052679 filed Feb. 10, 2015 which designated the U.S. and which claims priority to European App. Serial No. 14154766.1 filed Feb. 12, 2014. The noted applications are incorporated herein by reference.

FIELD OF INVENTION

The present invention relates to a process to extract a phosgene compound from a gas stream.

In addition, the present invention relates to a process for the conversion of an amine to the corresponding isocyanate component by phosgenation of the amine, wherein an effluent gas stream comprising a phosgene compound is removed and the phosgene compound is extracted from the effluent gas stream.

BACKGROUND OF THE INVENTION

In processes where amines are converted to isocyanates using phosgene, as is well known in the art, a disadvantage is that in the phosgenation process typically an excess of phosgene is used, or that the phosgenation typically does not consume all phosgene in the reaction mixture. Hence typically the reaction mixture, either gaseous or liquid and possibly containing solids, e.g. all components present in a solvent, comprises phosgene. In the process of conversion of an amine group to an isocyanate group also hydrogen chloride is obtained and found in the reaction mixture.

Often the hydrogen chloride is separated from the reaction, and can be used in other processes or as a feed to a chlorine recycling process, provided the hydrogen chloride is purified to meet the needs of its further use.

Often there is also a need to remove the phosgene from the reaction mixture so that the phosgene can be reused.

AIM OF THE INVENTION

It is an object of the present invention, amongst others, to separate phosgene from a gas stream comprising phosgene so that the phosgene can be reused. It is a further object of the present invention to separate phosgene from a gas stream comprising phosgene and hydrogen chloride (HCl), so that the phosgene and/or the remaining hydrogen chloride can be reused. It is a further object of the present invention separate phosgene from gas mixtures comprising phosgene and other gases such as carbon monoxide [CO], carbon dioxide [$CO_2$], nitrogen [$N_2$], hydrogen chloride [HCl] and/or chlorine [$Cl_2$].

It is a further object of the present invention to develop a process which can withstand aggressive chemicals and which is reliable for use in a fully continuous industrial scale operation process.

Yet another object is to separate phosgene from a gas stream in a continuous operation process such as processes for the conversion of an amine to the corresponding isocyanate component by phosgenation of the amine.

It is a further object to reduce the size or even avoid the need to use absorption towers, stripping columns, distillation towers and the like in a fully continuous operation process for making isocyanates, where phosgene is separated from a gas stream comprising phosgene and other gases such as hydrogen chloride, such as is described in WO2004056758 and WO2013026592.

SUMMARY OF THE INVENTION

The above objects, amongst others, are achieved, at least partially, if not completely, by a process according to claim 1.

The above objects, amongst others, are achieved at least partially, if not completely, by a process to extract a phosgene compound from an initial gas stream, comprising: providing a membrane extracting unit comprising at least one extracting cell that comprises at least one membrane contactor module comprising a membrane having at least two sides, a gas side and a liquid side; letting flow an initial gas stream comprising a phosgene compound on the gas side of the membrane contactor module; and letting flow an extractant liquid stream, suitable for dissolving a phosgene compound, on the liquid side of the membrane contactor module so that the extractant liquid stream absorbs the phosgene compound from the gas stream and provides a second extractant liquid stream enriched with the phosgene compound. Surprisingly, we have found that phosgene in a gas stream can enter a liquid stream comprising an extractant and mixes and/or dissolves in the extractant, using a membrane contactor module comprising a suitable membrane.

Surprisingly, it has been found that there are membranes that are suitable to allow extraction of the phosgene compound from a gas. Furthermore, it has been found that when the initial gas stream further comprises other gases, such as hydrogen chloride, the membrane is suitable to let through the phosgene compound that will be extracted in the extractant liquid and will dissolve in the extractant liquid while the other gases, such as HCl, substantially remain in the gas stream resulting in an extractant enriched with phosgene and a second gas stream depleted in phosgene.

The independent and dependent claims set out particular and preferred features of the invention. Features from the dependent claims may be combined with features of the independent or other dependent claims as appropriate.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Definitions and Terms

In the context of the present invention the following terms have the following meaning:

1) Except where explicitly stated differently, when reference is made to w % or wt % or % wt or "weight percent" of a component, this refers to the weight of this component over the total weight of the fluid or product in which the component is present at that moment, the ratio being expressed as percentage.
2) Unless otherwise indicated, the term "bara" is a reference to the absolute pressure expressed in the unit "bar", wherein 1 bar equals 100 kPa and 0.987 atm.
3) A membrane contactor module is a device comprising a membrane that allows a gas phase at a gas side and a liquid phase at a liquid side to come into contact with each other for the purpose of mass transfer between the phases without dispersing one phase into the other. The membrane contactor module comprises a membrane that is microporous and allows that subsequently no liquid passes through the pore into the gas side of the membrane. The membrane acts as a barrier between the gas phase and liquid phase and allows them to interface at the pores of the membrane.

4) According to this invention, hydrogen chloride i.e. HCl, refers to the compound as such. It does not refer to hydrochloric acid, which is the compound that comes in contact with water and is ionized.

5) According to this invention, a "phosgene compound" is a compound that is suitable to provide a phosgenation reaction and is preferably selected from the group consisting of phosgene (i.e. carbonyl dichloride or $COCl_2$), bromochlorophosgene (i.e. carbonyl bromide chloride or COBrCl) and dibromophosgene (i.e. carbonyl dibromide or $COBr_2$) or mixtures thereof.

6) According to this invention, there is no intention that the word "dissolves" would correspond unequivocally to the actual physical state of the phosgene compound molecules in the extractant liquid. As is used in the present invention, "dissolving" of the phosgene compound in the extractant, implies that the phosgene compound dissolves and/or mixes with the extractant liquid.

DETAILED DESCRIPTION

A first aspect of the present invention is related to a process for extracting a phosgene compound from an initial gas stream, comprising:
  providing a membrane extracting unit comprising at least one extracting cell that comprises at least one membrane contactor module having a membrane with at least two sides, a gas side and a liquid side;
  letting flow the initial gas stream comprising the phosgene compound on the gas side of the membrane; and
  letting flow an extractant liquid stream, suitable for dissolving the phosgene compound, on the liquid side of the membrane so that the extractant liquid stream absorbs the phosgene compound from the gas stream and provides a second extractant liquid stream enriched with the phosgene compound.

The membrane extracting unit is provided with at least two inflows and at least two outflows. The membrane extracting unit comprises at least one extracting cell that comprises at least one membrane contactor module unit. Each membrane extracting unit has at least one inflow for feeding the initial gas flow comprising a phosgene compound and at least one inflow for feeding the extractant and at least one outflow for a second gas stream and at least one outflow for the second extractant liquid stream that is enriched with the phosgene compound.

The membrane contactor module, and the membrane from this module have at least two sides, a gas side and a liquid side and divides the extracting cell in at least two parts, a gas part and a liquid part. The initial gas stream comprising a phosgene compound is fed to the gas part of the extracting cell and a liquid stream comprising the extractant is fed to the liquid part of the extracting cell. The membrane from the membrane contactor module contacts the initial gas on the gas side of the membrane contactor module and contacts the extractant liquid on the liquid side of the membrane contactor module. The membrane contactor module allows that the initial gas and the extractant liquid come into direct contact with each other at pores of the membrane of the membrane contactor module. At the pores of the membrane, an interface between the gas comprising the phosgene compound and the extractant liquid is created. At this interface, the phosgene compound dissolves in an extractant liquid. This results in a second extractant liquid at the liquid side that becomes enriched with the phosgene compound.

In one embodiment of this first aspect, the initial gas stream comprises a phosgene compound and a second gas compound selected from the group consisting of carbon monoxide, carbon dioxide, hydrogen chloride, nitrogen and/or chlorine. The extractant liquid is a better solvent for the phosgene compound than for the second gas compound. Due to the difference in solubility of the phosgene compound and the gas compound, the phosgene compound will dissolve in the extractant liquid at the pore of the membrane contactor module, while the gas compound remains substantially at the gas side. It is recognized that in practice some gas may also pass through the membrane. The process of this embodiment provides besides a second extractant liquid stream enriched with the phosgene compound, also a second gas stream depleted in the phosgene compound and enriched with the gas compound(s) compared with the initial gas stream. One outflow of the extracting unit in this embodiment is for the second gas stream which is depleted in the phosgene compound.

A preferred second gas compound is HCl. A preferred phosgene compound is phosgene ($COCl_2$). A gas mixture of HCl and phosgene is often provided in a process for making isocyanates. It is often required to separate the HCl from the phosgene so that the phosgene can be reused and HCl is purified from the gas mixture.

Another preferred second gas compound is a combination of CO and $Cl_2$. Phosgene is made from CO and $Cl_2$ in a reaction, providing a mixture of phosgene, unreacted $Cl_2$ and excess CO. The process according to the invention can be used to extract phosgene from that mixture so that the phosgene can be used for other purposes, such as the provision of isocyanates.

Preferably, the membrane contactor module only represents an interface or barrier between the incoming initial gas stream containing the phosgene compound and/or the gas compound at the gas side of the membrane and the liquid extractant at the liquid side of the membrane.

Accordingly, in case that the initial gas stream further comprises a second gas compound, the membrane extracting process provides a separation between the phosgene compound and the second gas compound. The membrane does not provide selective separation between the gases by e.g. selectively letting through only one specific compound. Separation occurs because of the different solubility between the phosgene compound and the second gas compound in the extractant. The phosgene compound has a higher solubility in the extractant than the second gas compound, which has a low solubility in the extractant.

Accordingly, the extractant liquid has a higher solubility capability for the phosgene compound than for the second gas compound.

A suitable extractant liquid is one that produces a relative volatility α which is a ratio of K-values [K1/K2], of between 0.02 and 0.08, preferably between 0.03 and 0.07, most preferably between 0.04 and 0.06, between the phosgene compound and the second gas compound,
  wherein K1 is the concentration of the phosgene compound in the gas phase, divided by the concentration of the phosgene compound in the liquid phase, $$K1 = \frac{[\text{phosgene compound}]\text{gas}}{[\text{phosgene compound}]\text{liquid}}; K2 = \frac{[\text{second gas compound}]\text{gas}}{[\text{second gas compound}]\text{liquid}}$$

and
wherein K2 is the concentration of the second gas compound in the gas phase divided by the concentration of the second gas compound in the liquid phase,
when the extractant liquid, the second gas stream and the phosgene compound are in a non dynamic system at 1 bar and at 0° C.

A suitable phosgene compound has a K1 value of between 0.70 and 1.40, preferably between 0.9 and 1.3 when the extractant liquid, the second gas stream and the phosgene compound are in a non dynamic system at 1 bar and at 0° C.

A suitable second gas compound has a K2 value of between 8.7 and 70, preferably between 10 and 46 when the extractant liquid, the second gas stream and the phosgene compound are in a non dynamic system at 1 bar and at 0° C.

A suitable extractant liquid has a K3 value of between 0.001 and 0.015, preferably between 0.003 and 0.007, wherein $$K3 = \frac{[\text{extractant liquid}]\text{gas}}{[\text{extractant liquid}]\text{liquid}}$$

when the extractant liquid, the second gas stream and the phosgene compound are in a non dynamic system at 1 bar and at 0° C.

For example, in a system wherein the phosgene compound is phosgene, the second gas is HCl and the extractant liquid is MCB, the phosgene and HCl have relative volatility [α] which is a ratio of K-values [K1/K2] of about 0.046 at 1 bar and at 0° C., wherein K1 is the concentration of phosgene in the gas phase divided by the concentration of phosgene in the liquid phase and K2 is the concentration of HCl in the gas phase divided by the concentration of HCl in the liquid phase mixture; wherein K1 is about 0.88 at 1 bar and at 0° C. and K2 is about 19.3 at 1 bar and at 0° C.; and wherein MCB has a K-value K3 of about 0.0041 (at 1 bar and 0° C.), where K3 is the concentration of MCB in the gas phase divided by the concentration of MCB in the liquid phase mixture.

This means that at 1 bar and at room temperature most of the phosgene compound is dissolved in the extractant liquid. Preferably, between 90 and 99.9 wt %, preferably between 95 and 99 wt % of the phosgene compound is dissolved in the extractant liquid. The second gas stream substantially does not dissolve in the extractant liquid. Preferably, less then 10 wt %, preferably between 5 and 0% of the second gas stream is found in the extractant liquid. Other examples may be deducted from "Yow-Lin Huang, Manfred Heilig, Hans Hasse, Jadran Vrabec, AIChE Journal Vol 57 (2011) 1043-1060; Vapor-liquid equilibria of hydrogen chloride, phosgene, benzene, chlorobenzene, orthodichlorobenzene, and toluene by molecular simulation." This reference is included in its entirety.

Preferably, the extractant does not dissolve the membrane of the membrane contactor module. Preferably, the extractant liquid is chosen so that it does not interfere in other processes for which the extracted phosgene compound is used. E.g. MCB is a suitable extractant for extracting phosgene, and MCB enriched with phosgene can be used in a process to provide isocyanates.

In one embodiment, the extractant liquid is an inert aromatic, aliphatic or cyclic hydrocarbon or halogenated derivative thereof. Examples of extractant liquid are aromatic compounds such as monochlorobenzene or dichlorobenzene, for example orthodichlorobenzene, toluene, xylene, naphthalene derivatives such as tertralin or decalin, alkanes having from about 5 to about 12 carbon atoms, e.g. hexane, heptane, octane, nonane or decane, cycloalkanes such as cyclohexane, largely inert esters and ethers, e.g. ethyl acetate or butyl acetate, tetrahydrofuran, dioxane or diphenylether. Most preferably, the extractant is selected from the group consisting of monochlorobenzene, dichlorobenzene, cyclohexane and toluene. The most preferred extractant liquid is MCB.

Preferably, the gas pressure at the gas side of the membrane contactor module has a higher pressure than on the liquid side of the membrane contactor module. The pressure difference between the two sides can improve the absorption of the phosgene compound from the gas side into the extractant. Preferably the pressure at the gas side is 0.1 to 5 bara more than the pressure at the liquid side.

For example, the pressure at the gas side is above atmospheric, while the pressure at the liquid side of the membrane is atmospheric or sub-atmospheric. A pressure above atmospheric in the range of 1.2 to 4 bara is preferably applied to the gas side, whereas at the liquid (extractant) side, a pressure of 0.1 to 1.9 bara is preferably applied.

A sweep gas may additionally be provided to the initial gas stream. The sweep gas helps to adjust the pressure and/or the inflow rate for the initial gas stream. Examples of suitable sweep gases are nitrogen and carbon dioxide.

The membrane of the membrane contactor module can take several forms. E.g. the membrane can be a flat sheet or a hollow fiber membrane such as Eclipse Membranes™ from Markel Corp.™.

Preferably, the membrane contactor module comprises a membrane that is made of microporous material. The pore size quoted by membrane manufactures can vary and depends on the type of chemicals that are used to perform the process. E.g. a pore size of the membrane can enlarge or shrink once it is in contact with the extractant and this enlargement or shrinking depends on the type of membrane and/or on the type of extractant that is used. Also the form of the pores can vary. Depending on the manufacturing of the membrane, the pores can have a uniform form or can have forms that vary for every pore. E.g. the form may have an essentially circular shape or a shape that is rather oval. The actual performance of the membrane in any specific environment depends on the pore size of the membrane and the form of the pore amongst other characteristics e.g. thickness, hydrophobicity, etc.

Preferably, the membranes of the membrane contactor modules have a mean pore size diameter of between 0.03 and 0.3 μm, and are preferably about 0.05 μm, wherein the pore sizes are measured using a capillary flow porometer e.g. from Porous Materials, Inc with a compressed gas. Furthermore, the actual performance of the membrane contactor module depends on other operating conditions, such as the temperatures of the initial gas stream and the extractant, the pressure that is applied on the membrane contactor module, the flow rate of the initial gas stream and the liquid stream and the effective surface of the membrane. In addition, the performance of the membrane contactor module may also depend on design elements of the membrane contactor module such as use of flat sheet membranes or hollow fiber membranes, geometry and orientations of inlets, outlets, baffles, heating or cooling elements and the like. The membrane of the membrane contactor module allows letting through gas to the liquid side, while it inhibits that the extractant comes through the membrane. In addition, the membrane allows that pressure can be built up on the gas side of the membrane contactor module. To obtain this, a combination of the pore size, the thickness of the membrane and the type of material can make a membrane suitable to carry out the process of the invention.

The membranes of the membrane contactor module may have an average thickness of between 15 µm and 120 µm. Membranes that are thinner may not be suitable since they can let through some of the extractant liquid and/or may impede that a pressure is built up at the gas side of the membrane. The thickness of the membrane is measured using an "Inspect" scanning electron microscope (FEI Corporation).

Preferably, the membrane of the membrane contactor module is polymeric, ceramic, a composite or other types. Preferably polymeric membranes are used.

Preferably, the membrane of the membrane contactor module is hydrophobic. Good examples of suitable membranes are hydrophobic membranes made of polypropylene, polytetrafluoroethylene (PTFE), polyvinylidene fluoride (PVDF), silicone rubber.

Design or selection of the industrial scale membrane contactor can be undertaken to take account of numerous parameters such as, but not limited to, the exact characteristics of the selected membrane, the flow rates of the different fluid streams, the physical properties of the different fluid streams, the chemical properties of the different fluid streams, the actual compositions of inlet streams and target compositions of outlet streams, possible presence of potentially fouling trace solid impurities, desired working temperatures and pressures and the like. For example, for hollow fibre membranes, the gas flow may be directed through the fibres with the extractant liquid flowing on the outside of the fibres or vice versa and flows may be counter-current, co-current or cross-flow. Additional mixing devices may also be added within the module. Examples of membrane contactors of general suitability include those provided by suppliers such as Membrana GmbH, Compact Membrane Systems Inc. or Markel Corporation although, of course, design, fabrication, installation and the like would be specifically tailored to meet the demands of the present invention.

The membrane contactor module can itself be provided with additional engineered containment structures fabricated from suitable materials such as but not limited to various grades of steel including speciality stainless steels, engineered polymers or plastics, ceramics, composites and the like.

In one embodiment the initial gas stream may further comprise traces of a solvent. Traces of solvent is to be understood as an amount of solvent in the range of 1 ppm to 1 w %, preferably 1 ppm to 100 ppm.

In one embodiment, the process further comprises a step of analyzing the concentrations of the gas compound and/or the phosgene compound in the initial gas stream and/or in the second gas stream depleted in phosgene. In one embodiment, the process further comprises a step of analyzing the concentrations of the extractant liquid and the phosgene in the extractant enriched with phosgene.

The compositions of the initial gas stream, the second gas stream, liquid extractant stream and/or the second liquid extractant stream enriched with the phosgene compound can be determined. More in particular, the concentration of the phosgene compound, the extractant and/or the gas compound can be determined. The determination can be carried out by one or more on-line analysis techniques such as spectroscopic or chromatographic techniques (Near Infrared spectroscopy, infra-red spectroscopy, gas chromatography) in order to monitor the performance of the unit. In situations where streams are simple binary mixtures of two components or close to pure binary systems then direct measurements of physical properties such as density, viscosity and the like can be used via calibration. These data in combination with for example temperature measurement will provide the ratios of the two major constituent components in the different streams. In particular the gas compound, the phosgene compound in the initial gas stream and the phosgene compound and gas compound concentration in the second outflow gas stream can be monitored by on-line FT-IR spectroscopy. The results from the on-line analysis can be used to monitor the effectiveness of the process. If necessary, several aspects of the process and equipment control can be adjusted either automatically or with manual intervention.

It is to be understood that when the embodiments form part of an industrial process, the initial gas stream can comprise further components e.g. phenyl isocyanate, or solvents such as MCB, which are in gas form.

According to some embodiments, the second gas stream of the membrane extracting unit may be further distilled and/or stripped and/or washed with a solvent thereby further reducing the content of the phosgene compound and/or the second gas compound. This solvent may be the same or different to the extractant used in the membrane extracting unit.

According to some embodiments, the process can comprise a further step of separating the extractant liquid stream enriched with phosgene. This embodiment can be used in case that some of the second gas compound passes through the membrane contactor module. Substantially the entire gas compound does not dissolve in the extractant liquid, so that the gas and the liquid can be easily separated through a gas/liquid separator.

In another embodiment, the second gas stream depleted in the phosgene compound is partially recycled or blended with the initial gas stream for feeding it back to the inflow at the gas side.

In another embodiment, the second extractant liquid stream enriched with the phosgene compound is partially recycled and/or blended with the extractant liquid.

In case the membrane extracting unit comprises several extracting cells, the outflowing second gas stream from a preceding extracting cell may be the inflow for a subsequent extracting cell in order to improve the separation efficiency.

In case the membrane extracting unit comprises more than one extracting cell, these cells may be coupled to each other in parallel, i.e. the initial gas flow stream is used as feed for all extracting cells.

In another embodiment, alternatively, these more than one cells may be coupled in series. In its most simple form, the initial gas stream is used as feed for the first cell of the N cells in series, the feed of each subsequent cell is the outflowing gas flow of the previous cell.

In yet another embodiment, the membrane extracting cell comprises means to avoid condensation of the gas stream in subsequent cells. E.g. condensers or heaters may be provided between consecutive cells. Alternatively or additionally, the cells have means to provide temperature control, e.g. heating and/or cooling means.

According to a second aspect of this invention a process is provided for the conversion of an amine to the corresponding isocyanate component by phosgenation of the amine, the process comprising the steps of:
provide a reaction mixture comprising an amine and phosgene to a phosgenation reactor;
at least partially converting the amine and the phosgene in the reaction mixture into the corresponding isocyanate component and hydrogen chloride, thereby providing a liquid isocyanate stream comprising the isocyanate component, phosgene and hydrogen chloride;
removing at least part of the phosgene and at least part of the hydrogen chloride from the liquid isocyanate stream as a removed gas stream;
optionally, partially condensing the removed gas stream providing a liquid intermediate mixture and a gas stream coming from the partially condensing step;
optionally, distilling and/or stripping and/or washing with a solvent of the gas stream coming from the partially condensing step and/or the liquid intermediate mixture to provide a gaseous vent mixture comprising hydrogen chloride and phosgene;
providing an initial gas stream comprising phosgene and hydrogen chloride, which is the removed gas stream or which is the gas stream coming from the partially condensing step or which is the gaseous vent mixture, or a combination thereof;
extracting phosgene from the initial gas stream according to the first aspect of the invention, wherein the gas compound is hydrogen chloride, providing a second gas stream depleted in phosgene and an extractant enriched with phosgene.

It is to be understood that the embodiments and the preferred features as well as the advantages for the embodiments and the preferred features as described above for the first aspect of the invention apply mutatis mutandis for this aspect of the invention.

The process may be applied in processes for converting virtually any amine to its corresponding isocyanate through phosgenation. The processes are suitable for use in the phosgenation of e.g. toluene diamine (TDA) to toluene diisocyanate (TDI), hexamethylene diamine (HDA) to hexamethylene diisocyanate (HDI), isophorone diamine (IPDA) to isophorone diisocyanate (IPDI), methylenedicyclohexylamine (H12MDA) to methylenedicyclohexylisocyanate (H12MDI). It is understood that the amines mentioned may be used in crude form, i.e. as mixtures of isomers and other components obtained by the production process to provide the amine as well known in the art.

Preferably, the amine is crude methylene-bridged polyphenyl polyamines (also referred to as MDA). This crude methylene-bridged polyphenyl polyamines typically is a mixture of the isomers of methylene diphenylene diamine (so called 2,2'MDA, 2,4'MDA and 4,4'MDA), in combination with methylene-bridged polyphenyl polyamines comprising more than 2 phenyl and more than 2 amine groups in their structure. This crude methylene-bridged polyphenyl polyamines typically is prepared from aniline, or aniline derivatives, by reacting them with formaldehyde in the presence of a solution of a strong acid such as, for example, hydrochloric, sulfuric or phosphoric acid. Formaldehyde may be provided in various forms, preferably as an aqueous solution. Solid acid catalyzed processes are also known.

Preferably, the reaction mixture further comprises a solvent. It is possible to use solvents which are generally suitable for the preparation of isocyanates. These are preferably inert aromatic, aliphatic or cyclic hydrocarbons or halogenated derivatives thereof. Examples of such solvents are aromatic compounds such as monochlorobenzene or dichlorobenzene, for example orthodichlorobenzene, toluene, xylene, naphthalene derivatives such as tertralin or decalin, alkanes having from about 5 to about 12 carbon atoms, e.g. hexane, heptane, octane, nonane or decane, cycloalkanes such as cyclohexane, largely inert esters and ethers, e.g. ethyl acetate or butyl acetate, tetrahydrofuran, dioxane or diphenylether. Most preferably, the solvent is selected from the group consisting of monochlorobenzene, dichlorobenzene, cyclohexane and toluene. The solvent is typically used to facilitate the phosgenation of the amines in liquid form and is typically used to dissolve the amine and the phosgene before mixing and reacting these two components. When a solvent is used, the extractant enriched with phosgene can be recycled for the conversion of amine and phosgene to isocyanate and hydrogen chloride.

A person skilled in the art knows that phosgenation reaction can occur in a gas phase. Typically, a solvent may be used in a quenching phase and/or in a work up phase of the reaction. Recycling of the phosgene and solvent is also possible when phosgenation occurs in a gas phase, however, the phosgene solvent mixture should be treated first by separating the phosgene, which can be used for the phosgenation, and the solvent, which can be used for the quenching phase or work up phase.

Preferably, the removed gas stream, removed from the liquid isocyanate stream typically comprises 15 to 50 wt % phosgene, 30 to 80 wt % hydrogen chloride, and 0.01 to 40 wt % solvent. The gas stream in the isocyanate stream that is removed, is provided at temperatures of above 75 deg C., typically in the range of −30 to 160 deg C. Typical pressure of the gaseous mixture is in the range of 2 to 40 bara.

According to some embodiments, condensing may include cooling the gaseous mixture to a temperature in the range of 60 to 20 deg C., the cooling may be conducted in subsequent stages. According to some embodiments, condensing may include cooling the gaseous mixture to a temperature in the range of 20 to −40 deg C., the cooling may be conducted in subsequent stages.

Using the process according to the present invention for the conversion of an amine to the corresponding isocyanate component thereby using the membrane extracting unit may finally result in a stream of hydrogen chloride depleted in phosgene, which is substantially pure hydrogen chloride or substantially free of phosgene. Substantially pure hydrogen chloride means that the fluid comprises 1 ppm to 0.1 w %, preferably 1 ppm to 100 ppm of phosgene.

The substantially pure hydrogen chloride may be used in other chemical processes run on the same chemical plant. Alternatively this hydrogen chloride may be transported to remote operations, or may be used to provide hydrochloric acid, by combining the hydrogen chloride with water.

As an example, in case the isocyanate made is methylene diphenylene diisocyanate (MDI), the hydrogen chloride may be partly recycled to the production facility (as gaseous hydrogen chloride or as liquid HCl) where aniline and formaldehyde are condensed to methylene diphenylene diamine, the precursor amine of the present process for the conversion of an amine to the corresponding isocyanate component by phosgenation of said amine. These processes are known by a person skilled in the art.

FIGURES

Figure 1:
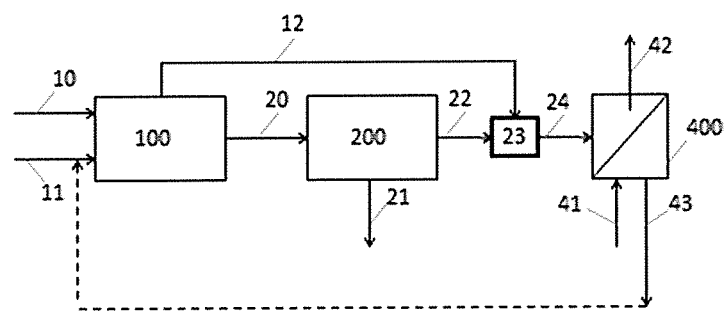
FIGS. 1, 2, 3 and 4 are schematic views of processes for the conversion of amine to the corresponding isocyanate component according to the invention comprising an extractant unit as described.

FIG. 1 shows schematically a process for the conversion of an amine, e.g. MDA, to the corresponding isocyanate component, e.g. MDI, by phosgenation using a phosgene compound of this amine which process flow comprises the membrane extracting unit according to the invention. A reaction mixture comprising the amine and the phosgene compound is provided to a phosgenation reactor 100. This is done by providing the amine dissolved in a solvent, such as MCB, through stream 10 and the phosgene compound, such as phosgene, dissolved in a solvent, such as MCB, through stream 11. Typically an excess of the phosgene compound is provided in reactor 100. The reactor may be, as is known in the art, a series of consecutive reactors, through which the reaction mixture passes one after the other. At least part of the amine is converted to the isocyanate, thereby producing hydrogen chloride. At the end of the reaction in the reactor 100, a liquid isocyanate stream 20 comprising the isocyanate component, the excess or non reacted phosgene and hydrogen chloride in the solvent is obtained.

The liquid isocyanate stream 20 is subjected to distillation and stripping to remove part of the solvent and residual traces of phosgene and HCl in unit 200, thereby providing a gaseous mixture 22 comprising phosgene and hydrogen chloride, and a small part of the solvent being MCB. The isocyanate and the rest of the solvent MCB is recovered as stream 21. Some HCl and some phosgene may be obtained directly from reactor 100 through stream 12 and may form part of the initial gas stream. Stream 22 comprising HCl, the phosgene compound and MCB in a gaseous phase, optionally together with stream 12, form the initial gas phase 23 and are provided 24 to the gas side of the membrane extracting unit 400 so that the gas stream contacts the gas side of the membrane contactor module.

An extractant stream 41, preferably a MCB stream, is fed at the liquid side of the membrane extracting unit so that the extractant contacts the liquid side of the membrane contactor module. As such, there are provided (i) a gaseous mixture depleted in phosgene 42 in an outflow of the membrane extracting unit and (ii) an extractant liquid enriched with the phosgene compound 43. The latter can be recycled and combined with fresh phosgene and optionally additional solvent to form stream 11, optionally after further treatment, and can be used for the phosgenation process.

The second gas stream depleted with phosgene 42 may be further used, e.g. by compression in a compressor after which the traces of MCB/phosgene can be removed from the compressed hydrogen chloride rich steam e.g. by condensing in a condenser to provide substantially solvent free hydrogen chloride gas and a combined phosgene-MCB stream (not illustrated).

Figure 2:
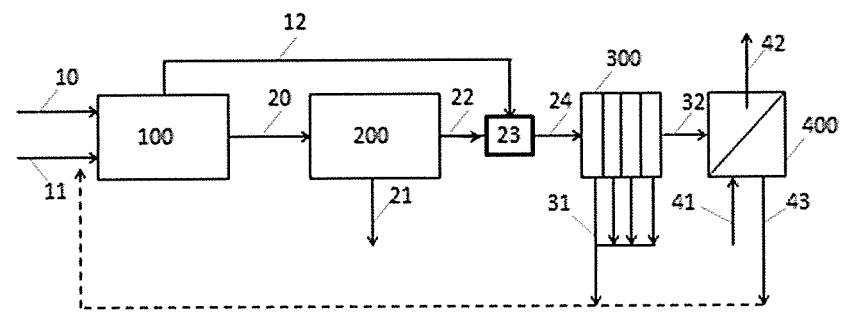

FIG. 2 shows schematically a process for the conversion of an amine, to the corresponding isocyanate component, which process flow comprises the membrane extracting unit according to the invention as is found in FIG. 1. In addition, FIG. 2 comprises a cooling train 300 between unit 200 and the membrane extracting unit 400.

The gaseous mixture 22 coming from unit 200 has a temperature of typically between 50 to 200° C. The gaseous mixture, optionally combined with stream 12, forms stream 24, which is cooled in a cooling train 300, where in consecutive stages, using ambient air cooling, ambient water cooling and cooling using one or more refrigerants, the temperature of the gaseous mixture is reduced to typically 100 to −35° C.

By cooling the gaseous mixture 24, the phosgene and the MCB condense and are taken off as stream 31, being the combination of various streams obtained between the different cooling stages. In this stream 31, also some hydrogen chloride may be present. This stream can be combined with stream 43 and recycled by combining with fresh phosgene and optionally additional solvent to form stream 11, optionally after further treatment, and can be used for the phosgenation process.

The cooled gaseous mixture 32 is then fed into the membrane extracting unit 400 according to the present invention.

Figure 3:
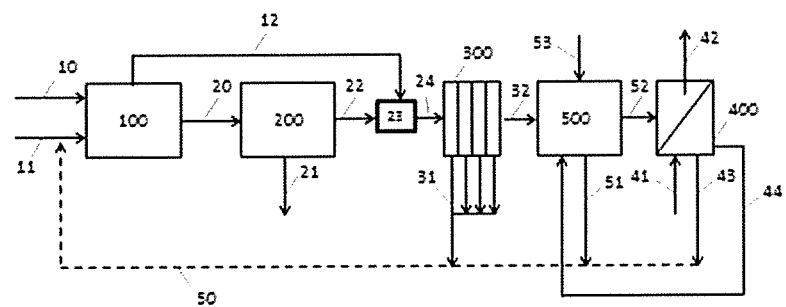

FIG. 3 shows schematically a process for the conversion of an amine, to the corresponding isocyanate component, which process flow comprises the membrane extracting unit according to the invention as is found in FIG. 2. In addition FIG. 3 shows a phosgene absorber with intermediate cooling 500. In the absorber the phosgene compound liquefies, while the HCl remains in the gas phase. It is possible to add extractant liquid 53 to the intermediate cooling device 500. The gas still comprises some phosgene gas and is fed as stream 52 to the extractant unit 400. At least part of the liquefied phosgene compound and at least part of the solvent, such as MCB, 51 can be combined with stream 43 and/or stream 31 and can be recycled, optionally after further treatment. Combination of these streams with fresh phosgene and optionally additional solvent can form stream 11 and can be used for the phosgenation process. At least part of the extractant enriched with the phosgene compound can enter again the phosgene absorber with intermediate cooling 500.

Figure 4:
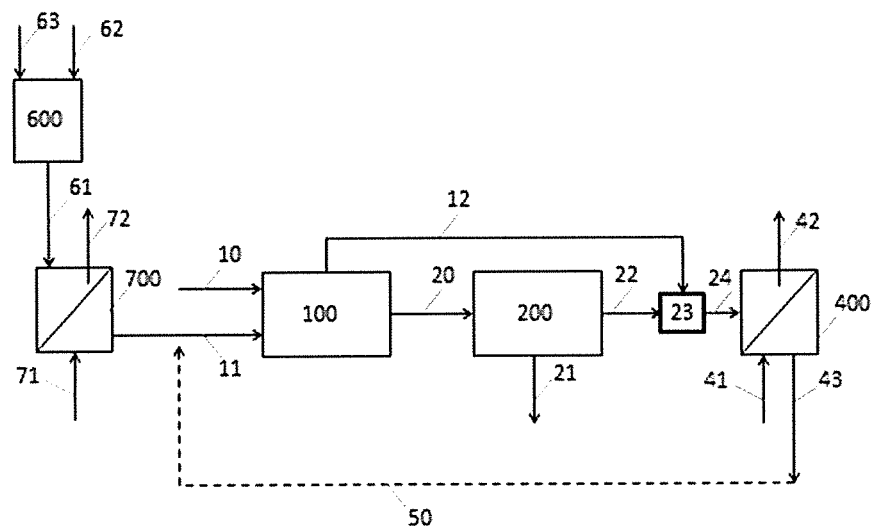

FIG. 4 shows schematically a process for the conversion of an amine, to the corresponding isocyanate component, which process flow comprises the membrane extracting unit according to the invention as is found in FIG. 1. In addition the figure shows the use of a second extractant unit 700 for extracting phosgene into an extractant such as MCB. Phosgene is made in a reactor 600 by reacting CO and $Cl_2$ that flow in the reactor unit 600 via inflow means 62 and 63. The reacted mixture 61 comprising phosgene, CO and $Cl_2$ streams is fed to extractant unit 700 at the gas side. MCB enters at the liquid side of the extractant unit 71. As such extractant liquid enriched with phosgene 11 is provided which can then enter in the reactor for converting amine into isocyanate 100. Also the gas compounds CO and $Cl_2$ depleted in phosgene 72 are provided.

EXAMPLES

Experimental

General Procedure

Figure 5:
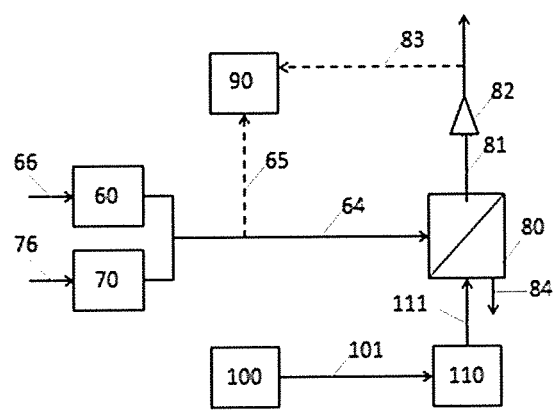
FIG. 5 is a schematic view of a lab set up used to facilitate the demonstration of the processes according to the invention.

The experiments were performed at room temperature using a set-up (FIG. 5) comprising:
- selectable feed systems for hydrogen chloride (HCl), phosgene ($COCl_2$) and nitrogen ($N_2$) 66 and 76;
- mass flow meters 60, 70 for controlling gas feed composition 64, i.e. the initial gas stream;
- an extractant (MCB) feed vessel 100 and an extractant stream 101 sent to a controllable pump 110;
- a polypropylene contactor module 80 containing a flat sheet membrane, dividing the module in a gas side and a liquid side; the effective [usable] membrane area within the module is 17.1×37.6 cm, inlet streams providing extractant 111 and feed stream 64, and outlet stream for the retentate 81, i.e. the second gas stream depleted in phosgene, or the permeate 84, i.e. the extractant enriched with phosgene.

an on-line infra-red spectrometer 90 for analyzing stream compositions provided with gaseous nitrogen [$N_2$] with which to dilute the feed 65 and retentate gas 83 streams to be analyzed when required and calibrated with known amounts of HCl and phosgene. The mass balance for phosgene and HCl could be confirmed by wet chemical measurements of the composition of the permeate in the outlet stream 84.

a pressure control valve 82 in the retentate line 81 various valves, connecting lines, pressure measuring devices and the like, including selectable lines and valves in order to be able to analyze the gaseous feed and retentate streams Example 1

Gaseous phosgene and HCl were fed [via the mass flow meters 60 and 70 respectively] along feed line 64 to the gas side of the membrane contactor module 80 which held a Tetratex® PTFE flat sheet membrane AX07-198 from Donaldson—nominal pore size of 0.05 micron and nominal average thickness of 17.8 μm. The flows used were about 200 ml/min COCl2 (~0.8 g/min) and about 530 ml/min HCl (~0.8 g/min). A pressure of 1.2 bara was maintained in the gas stream by means of the pressure control valve 82 in the retentate line 81. Liquid MCB was fed from the feed vessel 100 to the liquid side of the membrane using a gear pump 110; the MCB flow was varied between 25 and 100 ml/min. The feed and retentate gas streams 64 and 81 respectively were switched by means of valves [not shown] and diluted with nitrogen for analysis with the FTIR spectrometer. The results as determined using the FTIR analysis are reported in table 1.

TABLE 1

Phosgene and HCl measured in the retentate compared to the feed composition using the AX07-198 membrane

| P - gas bara | MCB Flow ml/min | gas stream | $COCl_2$ g/min | $COCl_2$ w/w % | HCl g/min | HCl w/w % |
|---|---|---|---|---|---|---|
| 1.2 | — | Feed | 0.817 | 50.0 | 0.818 | 50.0 |
| 1.2 | 25 | Retentate | 0.179 | 20.9 | 0.679 | 79.1 |
| 1.2 | 50 | Retentate | 0.059 | 8.9 | 0.606 | 91.1 |
| 1.2 | 100 | Retentate | 0.019 | 3.5 | 0.541 | 96.5 |

The table shows that phosgene could be preferentially extracted from the phosgene/HCl feed gas stream into the MCB stream, leaving highly purified HCl as the retentate gas stream. For example, with an MCB flow of 100 ml/min, about 98% of the original phosgene was extracted into the MCB, with the retentate gas stream comprising about 66% of the original HCl enriched to more than 96% purity.

Example 2

The same conditions as used in Example 1 were used to test Tetratex® membrane #1320 from Donaldson—nominal pore size of 0.20 micron and nominal thickness of xx microns. The results in Table 2 show that phosgene could be preferentially extracted from the phosgene/HCl feed gas stream into the MCB stream, leaving highly purified HCl as the retentate gas stream. For example, with an MCB flow of 100 ml/min, about 99% of the original phosgene was extracted into the MCB, with the retentate gas stream comprising about 33% of the original HCl enriched to nearly 98% purity.

TABLE 2

Phosgene and HCl measured in the retentate compared to the feed composition using the 1320 membrane

| P - gas bara | MCB Flow ml/min | gas stream | $COCl_2$ g/min | $COCl_2$ w/w % | HCl g/min | HCl w/w % |
|---|---|---|---|---|---|---|
| 1.2 | — | Feed | 0.813 | 49.7 | 0.822 | 50.3 |
| 1.2 | 25 | Retentate | 0.045 | 12.4 | 0.321 | 87.6 |
| 1.2 | 50 | Retentate | 0.017 | 5.0 | 0.318 | 95.0 |
| 1.2 | 100 | Retentate | 0.006 | 2.2 | 0.274 | 97.8 |

Example 3

Tetratex® membrane #1326 with nominal pore size of 0.07 micron and nominal thickness of xx microns was mounted in the stainless steel module. In the absence of MCB on the liquid side of the membrane, no pressure could be built up upon starting the gas feed. Upon feeding MCB to the liquid side of the membrane, breakthrough of the liquid to the gas side of the membrane occurred. These observations indicate that this membrane is not suitable for use according to the required features of the present invention.

Example 4

As in Example 1, gaseous phosgene and HCl were fed to the membrane contactor module which held an AX07-198 membrane. The flows used were about 200 ml/min COCl2 (~0.8 g/min) and about 1585 ml/min HCl (~2.3 g/min). A pressure of 1.2 bara was maintained in the gas stream by means of the pressure control valve in the retentate line. Liquid MCB was fed from the feed vessel to the other side of the membrane; the MCB flow was varied between 25 and 100 ml/min. The results in Table 3 show that phosgene could be preferentially extracted from the phosgene/HCl feed gas stream into the MCB stream, leaving highly purified HCl as the retentate gas stream. For example, with an MCB flow of 100 ml/min, about 62% of the original phosgene was extracted into the MCB, with the retentate gas stream comprising about 89% of the original HCl enriched to nearly 87% purity.

TABLE 3

Phosgene and HCl measured in the retentate compared to the feed composition using the AX07-198 membrane

| P - gas bara | MCB Flow ml/min | gas stream | $COCl_2$ g/min | $COCl_2$ w/w % | HCl g/min | HCl w/w % |
|---|---|---|---|---|---|---|
| 1.2 | — | Feed | 0.823 | 26.1 | 2.326 | 73.9 |
| 1.2 | 25 | Retentate | 0.466 | 17.6 | 2.184 | 82.4 |
| 1.2 | 50 | Retentate | 0.388 | 15.4 | 2.129 | 84.6 |
| 1.2 | 100 | Retentate | 0.311 | 13.0 | 2.074 | 87.0 |

Example 5

As in Example 1, gaseous phosgene and HCl were fed to the membrane contactor module which held an AX07-198 membrane. The flows used were about 200 ml/min COCl2 (~0.8 g/min) and about 534 ml/min HCl (~0.8 g/min). A pressure of 1.4 bara was maintained in the gas stream by means of the pressure control valve in the retentate line. Liquid MCB was fed from the feed vessel to the other side of the membrane; the MCB flow was varied between 25 and 100 ml/min. The results in Table 4 show that phosgene could be preferentially extracted from the phosgene/HCl feed gas stream into the MCB stream, leaving highly purified HCl as the retentate gas stream. For example, with an MCB flow of 100 ml/min, about 99% of the original phosgene was extracted into the MCB, with the retentate gas stream comprising about 63% of the original HCl enriched to nearly 98% purity.

TABLE 4

Phosgene and HCl measured in the retentate compared to the feed composition using the AX07-198 membrane

| P - gas bara | MCB Flow ml/min | gas stream | $COCl_2$ g/min | $COCl_2$ w/w % | HCl g/min | HCl w/w % |
|---|---|---|---|---|---|---|
| 1.4 | — | Feed | 0.815 | 50.0 | 0.816 | 50.0 |
| 1.4 | 25 | Retentate | 0.145 | 18.2 | 0.649 | 81.8 |
| 1.4 | 50 | Retentate | 0.043 | 7.0 | 0.575 | 93.0 |
| 1.4 | 100 | Retentate | 0.013 | 2.5 | 0.510 | 97.5 |

Example 6

As in Example 1, gaseous phosgene and HCl were fed to the membrane contactor module which held an AX07-198 membrane. The flows used were about 200 ml/min COCl2 (~0.8 g/min) and about 272 ml/min HCl (~0.4 g/min). A pressure of 1.2 bara was maintained in the gas stream by means of the pressure control valve in the retentate line. Liquid MCB was fed from the feed vessel to the other side of the membrane at about 100 ml/min. The results in Table 5 show that phosgene could be preferentially extracted from the phosgene/HCl feed gas stream into the MCB stream, leaving highly purified HCl as the retentate gas stream. More than 99% of the original phosgene was extracted into the MCB, with the retentate gas stream comprising about 38% of the original HCl enriched to nearly 99% purity.

TABLE 5

Phosgene and HCl measured in the retentate compared to the feed composition using the AX07-198 membrane

| P - gas bara | MCB Flow ml/min | gas stream | $COCl_2$ g/min | $COCl_2$ w/w % | HCl g/min | HCl w/w % |
|---|---|---|---|---|---|---|
| 1.2 | — | Feed | 0.817 | 66.1 | 0.419 | 33.9 |
| 1.2 | 100 | Retentate | 0.0024 | 1.45 | 0.160 | 98.55 |

Example 7

To illustrate selective extraction of phosgene compounds out of gases comprising at least a second compound with negligible or very limited solubility in the extractant such as CO, Cl2, N2 and the like, gaseous phosgene and nitrogen were fed to the membrane contactor module which held an AX07-198 membrane. The flows used were about 500 ml/min COCl2 (~1.94 g/min) and about 500 ml/min N2 (~0.6 g/min). A pressure of 1.2 bara was maintained in the gas stream by means of the pressure control valve in the retentate line. Liquid MCB was fed from the feed vessel to the other side of the membrane at about 1.8 ml/min. Analysis of the retentate stream showed that the phosgene flow had been reduced to ~1.57 g/min, illustrating that about 20% of the phosgene had been extracted into the MCB in these conditions.

These examples illustrate how variations of some of the important parameters in various embodiments of the present invention of extracting phosgene compounds from mixed gas streams by means of a membrane contactor module can be combined to achieve different end results. Of course, in this laboratory set-up, the effective membrane area remained constant and all experiments were carried out at room temperature but it is clear that different combinations of parameters could be used with different membrane areas and operating at different temperatures to achieve other desirable results. Larger scale tests with greater membrane areas, different pressures, different temperatures and the like can clearly be carried out to determine scale up factors for achieving defined target compositions for the retentate and/or permeate in solvent streams in relation to the nature of the feed gas stream.

The invention claimed is:

1. A process for extracting a phosgene compound from an initial gas stream, comprising:
    providing a membrane contactor module comprising a membrane, which membrane has at least two sides, a gas side and a liquid side;
    letting flow an initial gas stream comprising a phosgene compound and a second gas compound selected from the group consisting of hydrogen chloride, carbon monoxide, carbon dioxide, nitrogen, chlorine and a mixture thereof on the gas side of the membrane; and
    letting flow an extractant liquid stream, suitable for dissolving the phosgene compound, on the liquid side of the membrane contactor module so that the extractant liquid stream absorbs the phosgene compound from the initial gas stream and provides a second extractant liquid stream enriched with the phosgene compound and wherein a second gas stream depleted in the phosgene compound is provided from the gas side of the membrane and
    wherein the phosgene compound is more soluble in the extractant liquid stream than the second gas compound.

2. The process according to claim 1, wherein the phosgene compound is selected from the group consisting of phosgene ($COCl_2$), bromochlorophosgene (COBrCl), dibromophosgene ($COBr_2$) and a mixture thereof.

3. The process according to claim 1, wherein the extractant liquid produces a relative volatility α, which is a ratio of K-values [K1/K2], of between 0.02 and 0.08 between the phosgene compound and the second gas compound,
    wherein K1 is the concentration of the phosgene compound in the gas phase, divided by the concentration of the phosgene compound in the liquid phase, and
    wherein K2 is the concentration of the second gas compound in the gas phase divided by the concentration of the second gas compound in the liquid phase,
    when the extractant liquid, the second gas stream and the phosgene compound are in a non dynamic system at 1 bar and at 0° C.

4. The process according to claim 1, wherein the phosgene compound has a K1 value of between 0.70 and 1.40; and/or
    wherein the second gas compound has a K2 value of between 8 and 70; and/or
    wherein the extractant liquid has a K3 value of between 0.001 and 0.010, wherein $$K3 = \frac{[\text{extractant liquid}]\text{gas}}{[\text{extractant liquid}]\text{liquid}}$$

when the extractant liquid, the second gas stream and the phosgene compound are in a non dynamic system at 1 bar and at 0° C.

5. The process according to claim 1, wherein the extractant liquid is selected from the group consisting of monochlorobenzene, dichlorobenzene, cyclohexane and toluene.

6. The process according to claim 1, wherein a pressure is applied across the membrane contractor module such that the pressure at the gas side is higher than the pressure at the liquid side.

7. The process according to claim 6, wherein the pressure at the gas side is 0.1 to 10 bara more than the pressure at the liquid side.

8. The process according to claim 1, wherein the membrane contactor module comprises a microporous membrane having a pore size and a thickness such that the phosgene gas goes through the membrane from the gas side to the liquid side, while the extractant remains at the liquid side.

9. The process according to claim 1, wherein the membrane contactor module comprises a microporous membrane having a pore size and a thickness such that a pressure can be built up at the gas side of the membrane contactor module.

10. The process according to claim 1, wherein the membrane of the membrane contactor module is polymeric, ceramic, or a composite thereof.

11. The process according to claim 1, wherein the membrane of the membrane contactor module is hydrophobic and/or is made of polypropylene, polytetrafluoroethylene (PTFE), polyvinylidene fluoride (PVDF), silicone rubber, or a combination thereof.

12. The process according to claim 1, wherein the second gas stream depleted in the phosgene compound is distilled and/or stripped and/or washed with a solvent further reducing the content of the phosgene compound in the second gas stream.

13. The process according to claim 1, further comprising analyzing the concentrations of the second gas compound, the phosgene compound and/or extractant liquid in the second extractant liquid stream enriched with the phosgene compound and/or in the initial gas stream.

14. A process for the conversion of an amine to the corresponding isocyanate component by phosgenation of the amine, the process comprising the steps of:
providing a reaction mixture comprising an amine and phosgene to a phosgenation reactor;
at least partially converting the amine and phosgene in the reaction mixture into the corresponding isocyanate component and hydrogen chloride, thereby providing a liquid isocyanate stream comprising the isocyanate component, phosgene and hydrogen chloride;
removing at least part of the phosgene and at least part of the hydrogen chloride from the liquid isocyanate stream as a removed gas stream;
optionally, partially condensing the removed gas stream providing a liquid intermediate mixture and a gas stream coming from the partially condensing step;
optionally, distilling and/or stripping and/or washing with a solvent the gas stream coming from the partially condensing step and/or the liquid intermediate mixture to provide a gaseous vent mixture comprising hydrogen chloride and phosgene;
providing an initial gas stream comprising phosgene and hydrogen chloride, which is the removed gas stream or which is the gas stream coming from the partially condensing step or which is the gaseous vent mixture, or a combination thereof;
extracting phosgene from the initial gas stream according to claim 1, wherein the second gas compound is hydrogen chloride, and providing a second gas stream depleted in phosgene and second extractant liquid stream enriched with the phosgene compound.

15. The process according to claim 14, wherein the reaction mixture of an amine and phosgene further comprises a solvent selected from the group consisting of monochlorobenzene, dichlorobenzene, cyclohexane and toluene.

16. The process according to claim 15, wherein the second extractant liquid stream enriched with the phosgene compound is used as a part of the phosgene source in the reaction mixture for at least partially converting the amine and the phosgene compound into the corresponding isocyanate component and hydrogen chloride.

17. The process according to claim 14, wherein the second extractant liquid stream enriched with the phosgene compound is blended with the liquid intermediate mixture.

* * * * *